United States Patent [19]

Demail et al.

[11] Patent Number: 5,723,704
[45] Date of Patent: Mar. 3, 1998

[54] PROCESS FOR THE PREPARATION OF ALKYL CHLORIDES

[75] Inventors: Hervé Demail; Jean-Claude Schweickert, both of Vert Le Petit; Pierre Le Gars, Sorgues, all of France

[73] Assignee: Societe Nationale des Poudres et Explosifs, Paris Cedex, France

[21] Appl. No.: 779,245

[22] Filed: Jan. 3, 1997

[30] Foreign Application Priority Data

Jan. 24, 1996 [FR] France ................... 96 00777

[51] Int. Cl.$^6$ ............... C07C 19/00; C07C 17/16
[52] U.S. Cl. .............................. 570/241; 570/258
[58] Field of Search ........................ 570/241, 258

[56] References Cited

U.S. PATENT DOCUMENTS 5,241,086  8/1993  Mas et al. ................... 570/258
5,384,415  1/1995  Mas et al. ................... 570/258

FOREIGN PATENT DOCUMENTS 857350  11/1952  Germany.

OTHER PUBLICATIONS

Chemical Abstracts, vol. 100, No. 1, Jan. 2, 1984, Columbus, OH, US; abstract No. 5828u, Mitsui Toatsu Chemicals, Inc.: "Alkyl chlorides", p. 500; col. 1; XP002015553 & JP-A-58 144 328 (Mitsui Toatsu Chemicals, Inc.) Aug. 27, 1983.

Primary Examiner—Alan Siegel
Attorney, Agent, or Firm—Bucknam and Archer

[57] ABSTRACT

Process for the preparation of alkyl chlorides, characterized in that:

a) in a first stage a primary mono- or polyhydric alcohol, which has a $C_4$–$C_{30}$ carbon chain which is saturated, substituted or otherwise by one or more chlorine atoms and branched or otherwise and which may comprise one or more $C_5$–$C_7$ cycloalkyl groups, is reacted with gaseous hydrochloric acid in the absence of catalyst and at a temperature of between 80° C. and 170° C., until the degree of conversion of the alcohol functional groups is equal to or between 60 and 95 mol %, and b) in a second stage phosgene and a catalyst are introduced into the reaction mixture, the catalyst being chosen from the group consisting of hexaalkylguanidinium halides and their hydrohalides, quaternary ammonium halides, quaternary phosphonium halites, pyridine and pyridines substituted by one or more $C_1$–$C_6$ alkyl groups, at a temperature of between 80° C. and 160°C.

The alkyl chlorides thus prepared are obtained in a very high purity.

9 Claims, No Drawings

PROCESS FOR THE PREPARATION OF ALKYL CHLORIDES

The invention relates to an improved process for the preparation of alkyl chlorides from the corresponding primary alcohols and hydrochloric acid.

It is known to prepare alkyl chlorides from the corresponding alcohols by reacting gaseous hydrochloric acid with the alcohol in the presence of catalysts such as zinc chloride, amines and ammonium or phosphonium halides. However, these processes are not entirely satisfactory. The reaction period is often very long. Isomeric compounds are formed. To increase the yield and to shorten the reaction period, a very large quantity of catalysts is employed, for example approximately 27 mass %, as indicated in Chemical Abstracts CA 83: 27529. Nevertheless the conversion of the alcohol is never complete and the separation of the alcohol from the alkyl chloride is either impossible or extremely difficult because of the very close boiling points of the compounds. The distillation must be performed with columns which have very many trays. Obtaining alkyl chlorides of a very high purity is consequently either impossible or very lengthy and very costly.

There was consequently a need for a process for the preparation of alkyl chlorides which does not exhibit the disadvantages of the previous processes.

The subject-matter of the invention is a process for the preparation of alkyl chlorides, characterized in that:

a) in a first stage a primary mono- or polyhydric aliphatic alcohol, which has a $C_4$–$C_{30}$ carbon chain which is saturated, substituted or otherwise by one or more chlorine atoms and branched or otherwise and which may comprise one or more $C_5$–$C_7$ cycloalkyl groups, is reacted with gaseous hydrochloric acid in the absence of catalyst and at a temperature of between 80° C. and 170° C., until the degree of conversion of the alcohol functional groups is equal to or between 60 and 95 mol %, and b) in a second stage phosgene and a catalyst are introduced into the reaction mixture, the catalyst being chosen from the group consisting of hexaalkylguanidinium halides and their hydrohalides, quaternary ammonium halides, quaternary phosphonium halides, pyridine and pyridines substituted by one or more $C_1$–$C_6$ alkyl groups, at a temperature of between 80° C. and 160° C.

The process according to the invention enables the alcohol functional group(s) to be converted virtually completely into the chloride functional group. The chlorides can then be easily separated from the secondary products which may have been formed, for example by distillation. They are consequently obtained in a very high purity, higher than 98.5% in the case of some of them.

The alcohols which are of interest to be converted using the process according to the invention are the primary mono- or polyhydric aliphatic alcohols, in particular the $C_4$–$C_{30}$, preferably $C_4$–$C_{22}$, saturated, mono-, di- or trihydric ones in which the chain structure solely of carbon atoms. This chain may be linear or branched. It may also comprise one or more cycloalkyl groups such as the cyclopentyl, cyclohexyl and cycloheptyl groups. It may carry one or more chlorine atoms as substituents.

Examples of alcohols which may be mentioned are 1-butanol 1,4-butanediol, 1-hexanol, 1,6-hexanediol, 1-octanol, 8-chloro-1-octanol, 1,8-octanediol, cyclohexylmethanol, 1-dodecanol 1-hexadecanol, docosanol and 2-ethyl-1-hexanol.

The process is preferably used without solvent. When a solvent is employed, it is chosen from solvents which are inert towards the reactants, such as chlorinated aromatic solvents.

In the first stage the alcohol is reacted with gaseous hydrochloric acid, preferably at a pressure that is higher than atmospheric pressure, which may range up to an absolute pressure of 10 bars and in particular from 2 to 6 bars absolute.

The reaction temperature is between 80° C. and 170° C. and preferably between 100° C. and 150° C.

No catalyst is added to the reaction mixture. The formation of isomeric compounds is thus avoided.

The reaction period depends on the alcohol to be converted. It is generally several hours. When a degree of conversion of the alcohol functional groups which is equal to or between 60 and 95 mol %, preferably equal to or between 70 and 90%, is reached, the reaction is stopped.

An aqueous phase has been formed. The chloride obtained, the unconverted alcohol and, possibly, secondary products are present in the organic phase.

In the second stage phosgene and a catalyst are introduced into the reaction mixture, preferably after the aqueous phase has been removed, for example after phase separation by density.

Quaternary ammonium or phosphoniumhalides may be employed as catalysts. The halogen is chlorine or bromine, preferably chlorine. Examples of catalysts of this type which may be mentioned are trimethylbenzylammoniumchloride, tributylbenzylammonium chloride, tetrabutylammoniumchloride, tetrahexylammonium chloride, benzyltriphenylphosphonium chloride and tetrabutylammonium bromide.

Pyridine or a pyridine substituted by one or more $C_1$–$C_6$ alkyl groups, such as picoline, may also be employed to catalyse the reaction. In this class pyridine is preferably employed.

The preferred catalysts are hexaalkylguanidinium halides and their hydrohalides. The halogen may be chlorine or bromine. Chlorine is preferably chosen. The alkyl radicals, which may be identical or different, generally contain from 1 to 8 and preferably from 1 to 4 carbon atoms. Examples which may be mentioned are hexamethylguandinium chloride, hexaethylguanidinium chloride, hexabutylguanidinium chloride and their hydrochlorides. Hexabutylguanidinium chloride or its hydrochloride is suitable.

A quantity of 0.01 to 1 mol %, preferably from 0.05 to 0.5%, of catalyst is generally employed, relative to the molar quantity of hydroxyl groups remaining to be converted.

The catalyst is preferably added first of all to the reaction mixture, followed gradually by phosgene.

The quantity of phosgene which is introduced is generally from 1 to 3 mol and preferably from 1 to 1.5 mol per mole of hydroxyl groups remaining to be converted.

The reaction is performed at a temperature of 80° C. to 160° C. and preferably at a temperature of 100° C. to 150° C. It usually lasts from 2 to 15 hours. At the end of the reation the organic phase then contains practically no more alcohol.

After the remaining gases have been removed, the chlorides can, if necessary, be separated from the secondary products formed, such as ethers, for example by distillation with a column with a few trays, their boiling points being very different.

Using the process of the invention, the chlorides are obtained in a good yield and a very high purity, often higher than 98.5%.

Alkyl chlorides are known compounds which are very useful as such or as synthesis intermediates, especially for the stabilization of polymers and in the field of plant protection.

The examples which follow illustrate the invention without, however, limiting it.

EXAMPLE 1

Preparation of octyl chloride.

26.64 kg (205 mol) of 1-octanol are introduced into a 40-1 reactor with stirring and are heated to 125° C., and 7.1 kg (194.5 mol) of gaseous hydrochloric acid are added by means of a tantalum dip pipe over hours at an absolute pressure of between 3.9 and 4.5 bars, the temperature being maintained between 125° C. and 40° C. The mixture is cooled to 80° C. The residual gaseous hydrochloric acid is decompressed. The organic phase and the aqueous phase are separated by density separation. 28.96 kg of organic phase are then recovered, the mass composition of which, determined by gas phase chromato-graphic analysis (GC), is the following: octyl chloride 78.5%, octanol 16.5%, dioctyl ether 5%.

16.54 kg of the organic phase obtained above are introduced into a 25-1 reactor with stirring, 10 g (0.02 mol) of hexabutyguanidinium chloride hydrochloride are added and the mixture is heated to 100° C. 2.8 kg (28.3 mol) of phosgene are next introduced by means of a glass dip pipe, over 1 hour at a temperature of between 110° C. and 115° C., and the reaction mixture is then maintained at 115° C. for 3 hours. The excess phosgene and the hydrochloric acid formed are removed by degassing. 16.6 kg of organic phase are thus obtained, the mass composition of which, determined by GC analysis, is the following: octyl chloride 93%, octanol 0%, dioctyl ether 5%. 14.3 kg of octyl chloride are recovered by distillation, by means of a 2-m packed column (Raschig rings) (boiling point: 107°–112° C. at 50 mm Hg, yield: 82% based on the octanol introduced at the beginning of the process), the purity of which is 99.7% (determined by GC analysis).

EXAMPLE 2

Preparation of hexadecyl chloride.

50.14 kg (202 mol) of 1-hexadecanol are introduced into a 40-1 reactor, with stirring, are heated to approximately 130° C. and 5.2 kg of gaseous hydrochloric acid are introduced while the temperature is maintained in the region of 140° C. and the pressure between 4 and 4.5 bars. When the reaction is finished, the mixture is cooled to 80°–85° C. The reactor is decompressed and the organic phase and the aqueous phase are then separated by density separation. The mass composition of the organic phase is approximately 68% of hexadecyl chloride, 28% of residual alcohol and 4% of dihexadecyl ether (the ratio of the chloride to the alcohol having been determined by GC analysis and the ether content having been assessed by $^1$H NMR analysis).

Phosgene is then reacted in the organic phase at a temperature of 120°–125° C. in the presence of 28 g of hexabutylguanidinium chloride hydrochloride, 10.9 kg of phosgene being employed. The reaction mixture is maintained at this temperature for 5 hours. The excess phosgene and the hydrochloric acid formed are removed by degassing under vacuum. The organic phase obtained has the following mass composition, determined by $^1$H NMR analysis: hexadecyl chloride 89%, dihexadecyl carbonate 6.7%, dihexadecyl ether 4.2%.

EXAMPLE 3

Preparation of 2-ethylhexol chloride.

26 kg (200 mol) of 2-ethyl-1-hexanol are introduced into a 40-1 reactor, with stirring, are heated to approximately 110° C. and 4.75 kg of gaseous hydrochloric acid are introduced while the temperature is maintained in the region of 140° C. and the pressure between 3.8 and 4.8 bars. When the reaction is finished, the reaction mixture is cooled to 80°–85° C. The reactor is decompressed and then the organic phase and the aqueous phase are separated by density separation. 28.28 kg of organic phase are recovered, the mass composition of which, determined by GC analysis, is 53.6% of 2-ethylhexyl chloride, 41.8% of residual alcohol and 2.3% of di(2ethylhexyl)ether.

584 g of the organic phase obtained above are next phosgenated at a temperature of 110°–115° C. in the presence of 0.1 mol %, relative to the molar quantity of residual alcohol, of hexabutylguanidinium chloride hydrochloride, 205 g of phosgene being employed. The reaction mixture is maintained at this temperature for 3 hours and then the excess phosgene and the hydrochloric acid formed are removed by degassing under vacuum. The organic phase has the following mass composition, determined by GC analysis: 2-ethylhexyl chloride 74.5%, bis(2-ethylhexyl) carbonate 10.7%, 2-ethylhexyl chloroformate 9.7%, bis(2-ethylhexyl)ether 2.4%. 2-Ethylhexyl chloride, the purity of which (determined by GC analysis) is higher than 97%, is recovered by distillation.

We claim:

1. Process for the preparation of alkyl chlorides, characterized in that:
    a) in a first stage a primary mono- or polyhydric aliphatic alcohol, which has a $C_4$–$C_{30}$ carbon chain which is saturated, substituted or otherwise by one or more chlorine atoms and branched or otherwise and which may comprise one or more $C_5$–$C_7$ cycloalkyl groups, is reacted with gaseous hydrochloric acid in the absence of catalyst and at a temperature of between 80° C. and 170° C., until the degree of conversion of the alcohol functional groups is equal to or between 60 and 95 mol %, and
    b) in a second stage phosgene and a catalyst are introduced into the reaction mixture, the catalyst being chosen from the group consisting of hexaalkylguanidinium halides and their hydrohalides, quaternary ammonium halides, quaternary phosphonium halides, pyridine and pyridines substituted by one or more $C_1$–$C_6$ alkyl groups, at a temperature of between 80° C. and 160° C.

2. Process according to claim 1, characterized in that the first stage is performed at a pressure which is higher than atmospheric pressure.

3. Process according to claim 1, characterized in that the quantity of catalyst which is employed is from 0.01 to 1 mol % relative to the molar quantity of hydroxyl groups remaining to be converted.

4. Process according to claim 1, characterized in that the catalyst is added before the introduction of phosgene.

5. Process according to claim 1, characterized in that the phosgene is added gradually.

6. Process according to claim 1, characterized in that the aqueous phase formed during the first stage is removed before the second stage is performed.

7. Process according to claim 1, characterized in that the quantity of phosgene which is introduced is from 1 to 3 mol per mole of hydroxyl groups to be converted.

8. Process according to claim 1, characterized in that the catalyst is chosen from the group consisting of hexaalkhexylguanidinium halides and their hydrohalides.

9. Process according to claim 8, characterized in that the catalyst is hexabutylguanidinium chloride or its hydrochloride.

* * * * *